(12) United States Patent
Nussbaum et al.

(10) Patent No.: US 11,376,795 B1
(45) Date of Patent: Jul. 5, 2022

(54) SINTERING MONITORING METHOD

(71) Applicant: University of South Florida, Tampa, FL (US)

(72) Inventors: Justin Nussbaum, Knoxville, TN (US); Nathan Brad Crane, Lutz, FL (US)

(73) Assignee: University of South Florida, Tampa, FL (US)

( * ) Notice: Subject to any disclaimer, the term of this patent is extended or adjusted under 35 U.S.C. 154(b) by 266 days.

(21) Appl. No.: 16/518,342

(22) Filed: Jul. 22, 2019

Related U.S. Application Data

(60) Provisional application No. 62/734,524, filed on Sep. 21, 2018.

(51) Int. Cl.
  *B29C 64/393* (2017.01)
  *B33Y 50/02* (2015.01)
  *B33Y 10/00* (2015.01)
  *B29C 64/153* (2017.01)

(52) U.S. Cl.
  CPC .......... *B29C 64/393* (2017.08); *B29C 64/153* (2017.08); *B33Y 10/00* (2014.12); *B33Y 50/02* (2014.12)

(58) Field of Classification Search
  CPC ..... B29C 64/393; B29C 64/153; B33Y 10/00; B33Y 50/02
  See application file for complete search history.

(56) References Cited

U.S. PATENT DOCUMENTS

| 4,863,538 A | 9/1989 | Deckard |
| 4,938,816 A | 7/1990 | Beaman et al. |
| 7,088,432 B2 | 8/2006 | Zhang |

(Continued)

FOREIGN PATENT DOCUMENTS

WO 2019032224 2/2019

OTHER PUBLICATIONS

Nussbaum et al. (Evaluation of Processing Variables in Large Area Polymer Sintering of Single Layer Components; http://sffsymposium.engr.utexas.edu/sites/default/files/2016/064-Nussbaum.pdf (Year: 2016).*

(Continued)

*Primary Examiner* — Yung-Sheng M Tsui
(74) *Attorney, Agent, or Firm* — Meunier Carlin and Curfman LLC

(57) ABSTRACT

The disclosed subject matter relates to methods for monitoring or controlling a manufacturing process of a material by determining when a variation in surface characteristics takes place. Such surface characteristics correlates to the processing condition of the material and can include density, roughness, porosity, or planarity on a surface of the material. The methods can include herein can include directing a solvent or energy on a surface of the material to form an at least partially modified surface, directing light at an incident angle with respect to the at least partially modified surface, measuring one or more predetermined properties of light reflected from the at least partially modified surface, determining that the material is fully processed based on the measured predetermined property of the light reflected, and optionally adjusting a processing parameter of the manufacturing process in response to the measured predetermined property.

20 Claims, 1 Drawing Sheet

(56) References Cited

U.S. PATENT DOCUMENTS

| | | | |
|---|---|---|---|
| 7,884,948 B2* | 2/2011 | Miyoshi | G01B 11/303 356/600 |
| 8,383,985 B2 | 2/2013 | Twelves, Jr. et al. | |
| 2006/0180957 A1 | 8/2006 | Hopkinson et al. | |
| 2009/0206065 A1 | 8/2009 | Kruth et al. | |
| 2011/0089610 A1 | 4/2011 | El-Siblani et al. | |
| 2012/0139167 A1 | 6/2012 | Fruth et al. | |
| 2013/0295212 A1 | 11/2013 | Chen et al. | |
| 2014/0314613 A1 | 10/2014 | Hopkinson et al. | |
| 2015/0268099 A1 | 9/2015 | Craig et al. | |
| 2016/0184893 A1 | 6/2016 | Dave et al. | |
| 2016/0185048 A1 | 6/2016 | Dave et al. | |
| 2017/0087634 A1 | 3/2017 | Beacham, Jr. et al. | |
| 2020/0061710 A1* | 2/2020 | Nassar | B29C 64/268 |

OTHER PUBLICATIONS

Launhardt et al., Detecting surface roughness on SLS parts with various measuring techniques, Polymer Testing, vol. 53, Aug. 2016, pp. 217-226 (Year: 2016).*

Kruth, G. Levy, F. Klocke, and T. H. C. Childs, "Consolidation phenomena in laser and powder-bed based layered manufacturing," CIRP Annals—Manufacturing Technology, vol. 56, No. 2, pp. 730-759, 2007.

Levy, Gideon N., Ralf Schindel, and Jean-Pierre Kruth. "Rapid manufacturing and rapid tooling with layer manufacturing (LM) technologies, state of the art and future perspectives." CIRP annals 52.2 (2003): 589-609.

Conley, James G., and H. L. Marcus. "Rapid prototyping and solid free form fabrication." Journal of Manufacturing Science and Engineering, Transactions of the ASME 119.4B (1997): 811-816.

* cited by examiner

SINTERING MONITORING METHOD

CROSS-REFERENCE TO RELATED APPLICATIONS

This application claims the benefit of and priority to U.S. Provisional Application Ser. No. 62/734,524 filed on Sep. 21, 2018, the disclosure of which is expressly incorporated herein by reference in its entirety.

STATEMENT ACKNOWLEDGING OF GOVERNMENT SUPPORT

This invention was made with government support under grant no. CMMI1563037 awarded by the National Science Foundation. The Government has certain rights in the invention.

BACKGROUND

Existing technologies to monitor the surface of powder bed fusion additives generally include monitoring emitted light to track the temperature of the surface. While these technologies can be helpful in correlating process parameters, they do not provide information on the materials being processed, such as the phase of the materials, roughness of the material's surface, or its porosity. Additionally, when the surface temperature is below the Draper point (about 497° C.), which includes processing conditions of a majority of polymers, infrared imaging systems are generally required for tracking the temperature. However, these systems are much more expensive and provide lower spatial resolution than similarly priced visible light cameras.

The additive manufacturing industry lacks a quality method to monitor and/or control powder bed fusion technologies, especially those which expose large areas (>3.14 mm$^2$). What are needed are systems and methods for providing an in-situ, simultaneous area based feedback control signal during manufacturing processes. The systems and methods disclosed herein address these and other needs.

SUMMARY

In accordance with the purposes of the disclosed materials and methods, as embodied and broadly described herein, the disclosed subject matter, in one aspect, relates to methods of making materials. In specific aspects, the disclosed subject matter relates to methods for monitoring or controlling the manufacturing process of a material. Such manufacturing process can include an additive manufacturing process such as a melting process, a sintering process, a densification, or a smoothing process. The material used in the manufacturing process can comprise a powder material, a fibrous material, or a fabricated composite material. preferably, the material is a polymer material.

The methods disclosed herein can include directing a solvent from a solvent source or energy from an energy source on a surface of the powder material to form an at least partially modified surface, directing light from a light source at an incident angle with respect to the at least partially modified surface, measuring one or more predetermined properties of light reflected to a detector from the at least partially modified surface, wherein the measured predetermined properties correlate to a processing condition of the material, determining that the material is fully processed when a measured predetermined property of the light reflected reaches a target value, and optionally adjusting a processing parameter of the manufacturing process in response to the measured predetermined property.

Methods for monitoring or controlling surface treatment of a material, comprising directing a solvent from a solvent source or energy from an energy source on an exterior surface of the material to reduce or eliminate surface defects and smooth the exterior surface of the material; directing light from a light source at an incident angle with respect to the exterior surface of the material; measuring one or more predetermined properties of light reflected to a detector from the exterior surface of the material, wherein the predetermined properties correlate to a planarity of the material; determining that the material is planar when a measured predetermined property of the light reflected reaches a target value; and optionally adjusting a processing parameter of the surface treatment in response to the measured predetermined property are also disclosed.

In some examples, the method includes determining that the material is fully processed when a measured predetermined property of the light reflected reaches a minimum value or a maximum value. For example, it can be determined that the material is fully processed (such as sintered, melted, or planar) when a measured predetermined property of the light reflected is about zero at an incident angle that is not normal to the fully processed material and the incident angle is not equal to an angle of the detector, or the material is fully processed when a measured predetermined property of the light reflected is maximum at an incident angle equal to an angle of the detector, or a combination thereof.

The energy source can be selected from an electromagnetic beam or an image. In some examples, the energy source is an image such as from an image projector, an array of LEDs or lasers, or an effectively constant exposure obtained by repeatedly scanning a point source at high rate of speed over the layer of the material. The light source can be a laser beam, a focused light beam (such as from one or more lamps having reflectors that focus their energy onto the material), or a projected image. Preferably, the light source is a collimated or substantially (nearly) collimated light source. In some instances, the energy source and the light source can be the same. In other instances, the energy source and the light source are different. The light source can be at a wavelength that maximizes the change in reflectivity (contrast) from the modified and unmodified states. In some instances, it may be desirable to choose a wavelength of incident light at which the processed (such as fused, sintered, melted, or planar) material is at least partially transparent as reflected signal can be obtained from sub-surface defects such as pores in the unprocessed or partially processed material.

As described herein, the methods can be used to monitor or control a manufacturing process by determining when a variation in surface characteristics takes place. Such surface characteristics correlates to the processing condition of the material and can include density, roughness, or porosity on a surface of the material. The measured reflectance, which is preferably made for a plurality of angles of reflection, can be used to provide quantitative data regarding the surface characteristics of the material, or can be compared to a range of acceptable reflectance which has been predetermined by measuring the reflectance of a set of control samples with known surface characteristics.

In certain embodiments, the measurements can be measured by a detector which can detect and measure the predetermined property of light reflected from a surface of the material. Such predetermined properties can include the number of reflective spots, the spacing of light, or the intensity of light reflected from the surface. The detector is not limited and, in some examples, can be selected from a thermal camera, an optical camera, a line camera, or a point detector such as those including a photodetector/photodiode. The reflected light can be measured at one or a plurality of angles of reflection to obtain more data. When doing so, it may be determined that a fully processed material (which may have a planar, smooth surface) reflect greater amounts of light, while rough surfaces scatter light to a greater degree, with the degree of scattering differing at each wavelength. As such, it can be determined that the material is fully processed when a measured predetermined property of the light reflected is maximum at an incident angle equal to an angle of the detector. In other cases, the detector can be positioned so that light reflected off the fully processed material (such as a smooth surface) will not reflect to the detector. This is possible when the incident light is not normal to the processed surface and that the angle of the detector is not equal to the angle of incidence. In the preferred embodiment both the incident light and the detector may be positioned in the same. Accordingly, it can be determined that the material is fully processed when a measured predetermined property of the light reflected is about zero at an incident angle that is not normal to the fully processed material and the incident angle is not equal to an angle of the detector.

In some cases, the method includes adjusting a processing parameter of the manufacturing process in response to the measured predetermined property. Such processing parameters can comprise an intensity, spot size, pulse frequency, shape, pulse duration, or spot geometry of all or part of the energy source or variance thereof in a temporal or spatial domain.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

Figure 1:
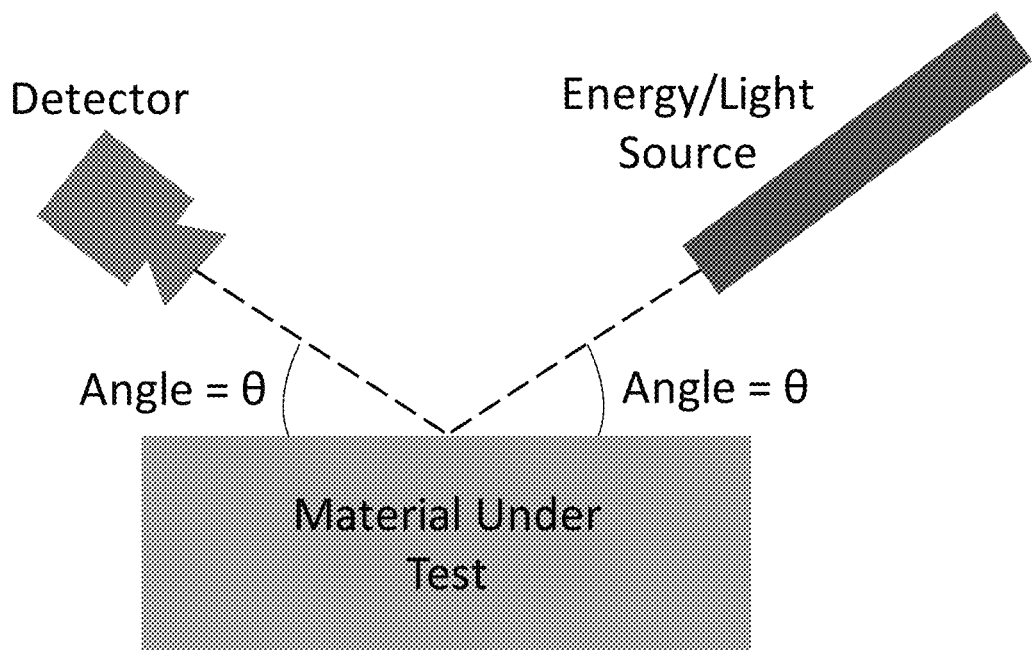
FIG. 1 is a schematic drawing showing an arrangement of the light and/or energy source, detector, and processed material. The incident angle of the light source is equal to the reflection angle of light to the detector. Accordingly, a measured predetermined property (such as intensity) of the light reflected from the fully processed material may exhibit maximum value, depending on the wavelength selected.
Figure 2:
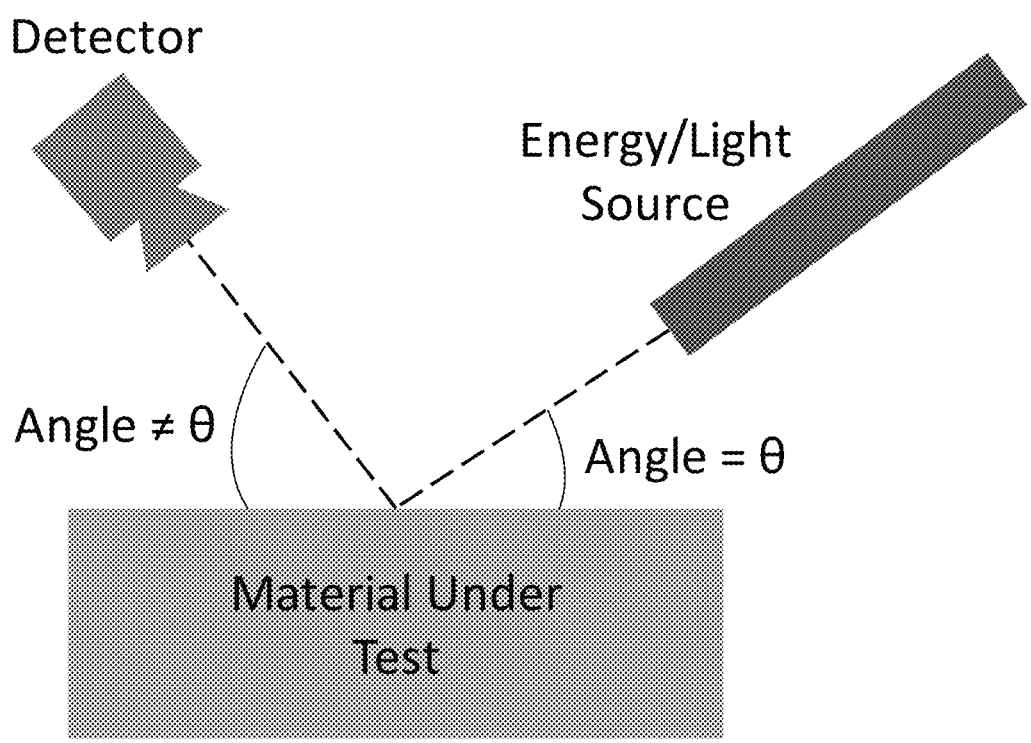
FIG. 2 is a schematic drawing showing an arrangement of the light and/or energy source, detector, and processed material. The incident angle of the light source is not normal to the processed material and the incident angle is not equal to the reflection angle of light to the detector. Accordingly, a measured predetermined property of the light reflected from the fully processed material would be about zero, or exhibit a minimum value depending on the wavelength selected.

The materials, compounds, compositions, and methods described herein may be understood more readily by reference to the following detailed description of specific aspects of the disclosed subject matter, the Figures, and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings: Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a polymer" includes mixtures of two or more such polymers, and the like.

As used herein, the term "substantially" refers to the complete or nearly complete extent or degree of an action, characteristic, property, state, structure, item, or result. For example, an object that is "substantially" collimated would mean that the light is either completely collimated or nearly completely collimated. The exact allowable degree of deviation from absolute completeness may, in some cases, depend on the specific context. However, generally speaking, the nearness of completion will be so as to have the same overall result as if absolute and total completion were obtained.

"Optional" or "optionally" means that the subsequently described event or circumstance can or cannot occur, and that the description includes instances where the event or circumstance occurs and instances where it does not.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

As used herein, the term "composition" is intended to encompass a product comprising the specified ingredients in the specified amounts, as well as any product which results, directly or indirectly, from combination of the specified ingredients in the specified amounts.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

Methods

Methods for controlling the manufacturing process of a material are disclosed herein. The methods can provide an in-situ, simultaneous area based feedback control signal which can be used to monitor and/or control various processing parameters during the manufacturing process. In some embodiments, the manufacturing process can include an additive manufacturing process. Such additive manufacturing process can include powder bed fusion processes for making parts formed from metal, ceramic, polymer, ceramic-metal composite, alloy, or other composite powder materials. Further additive manufacturing process can include surface treatment of a material, such as a surface smoothing process that may use a powdered or non-powdered material. For example, Fused Deposition Modeling (FDM) processes may deposit traces of material that can create a rippled surface. We have shown that heating and solvent exposure can smooth this surface. This method would be an appropriate way to monitor that surface. In this case it involves an AM process, but not a powdered material. There may also be applications that would just use a rough surface that was not created by AM—perhaps for a polymer that was machined. In both these cases, the exposure to heat or especially solvent needs to be monitored to avoid deforming the material and losing the geometric accuracy and this technique could be applicable Specific examples of polymer powder materials include polyphenylene sulfide, polyether ether ketones (PEEK), acrylonitrile butadiene styrene (ABS), polylactic acid (PLA), polycarbonates (PC), polystyrenes (PS) including styrene maleic anhydrides (SMA), polyketones, polyethers, poly ether ketone (PEK), poly ether ketone ketones, polyolefins, polyhydroxyalkanoates (PHA), polyacetals, polyesters including polyethylene terephthalates (PET) and polycaprolactones, polyoxyalkylenes, polyoxyalkylene/polyester copolymers, polyamides (PA) including nylons, polyolefins, polyvinyl chlorides (PVC), chlorinated polyvinyl chlorides (CPVC), polyvinylidene chlorides, acrylic resins, vinyl ester resins, phenolic resins, urea resins, melamine resins, epoxy resins, alkyd resins, polyalkyleneimines (e.g., polyethyleneimine), polyvinylpyrrolidone, polyallylamine, polyether polyamines (e.g., polyoxyethylene polyamine), or polyurethane elastomers, optionally copolymerized with comonomer units selected from ethylenically unsaturated carboxylic acids, ethylenically unsaturated carbonates, ethylenically unsaturated urethanes, ethylenically unsaturated alcohols, ethylenically unsaturated aromatics, alkyl acrylates, alkyl methacrylates, ethylene vinyl alcohols, vinyl acetates, styrenes, and hydroxyalkanoic acid, or blends thereof, copolymers thereof, derivatives thereof, or combinations thereof. Blends of the selected polymers may include blending the polymers with other powder materials. These powder materials may include, for example, at least one of glass beads, hollow glass spheres, other polymers, minerals, clays, flame-retardant additives, color additives, and/or other suitable materials.

Examples of suitable metal powders can include aluminum, aluminum alloys, titanium, titanium alloys, tungsten, tungsten alloys, vanadium, and vanadium alloys. Suitable ceramic materials can include aluminum oxide or alumina, zirconium oxide or zirconia, compact of particulate diamond, and/or pyrolytic carbon.

In other embodiments, the material used in the processes described herein can include a fibrous material or a fabricated composition material.

As described herein, the material may be in the form of a powder that absorbs light at one or more wavelengths of light from the energy (light) source. In an additional embodiment, the material may further include an absorber that absorbs light at one or more wavelengths of light from the energy source. Various absorbers could be added globally by premixing into the polymer material, or locally to help control the absorption areas of the material.

In some aspects, the disclosed methods can include directing energy from an energy source on a surface of the material to modify at least a surface of the material. In other aspects, the disclosed methods can include directing a solvent on a surface of the material to modify at least a surface of the material. The term "modify" as used herein can be used synonymously with the term "alter" or "change" and refers to a change in the surface characteristics or volume morphology of the starting material. For example, a "modified" material or surface can be formed from a process that induces densification, fusion, smoothing, or melting of the material by exposing them to heat.

The term "densify" or "densification" as used herein refers to the process of thermodynamically manipulating a material with the intent of increasing its density above that of a typical reference value, thereby increasing its energy storage potential. In the present case, the material can be densified by eliminating porosity that exists between particles in the material and is primarily driven by reduction of the surface energy of the particles. Densification can include melting and/or fusion of the powder material.

The term "fuse" or "fusion" as used herein refers to a state in which the starting material have adhered or physically bonded to one another by the application of heat causing a change in shape of the initial starting material and combining to create a larger mass. The material can be fused in the solid state (i.e., below the melting temperature), some in the liquid state after melting, and some through partial melting.

Fusion in the solid state is generally referred to as solid-state sintering. Sintering refers to a process in which the temperature of a material is raised to its softening point by thermal heating using an energy source, thereby causing the particles of the material to fuse together in the heated region. The temperature level needed for sintering depends on the material being sintered; but the higher the temperature is, the quicker it sinters. In some embodiments of the sintering process, an electromagnetic beam (e.g., laser beam) or an image at a substantially constant power level is incident on a material bed. A lateral layer of the part can be fabricated by repeated scanning of the laser beam in successive lines across a layer of material until the entire layer has been scanned. The laser is turned on at points where the material is to be sintered, otherwise, the laser is off. When one layer is complete, the surface of the sintering bed is lowered, another layer of polymer material is spread over the previous, now sintered layer, and the next layer is scanned. This process is repeated until the part is complete. The mechanism for sintering is primarily diffusion between material particles: because surface energy is proportional to total particle surface area, when particles reach sufficiently high temperatures, total surface area decreases in order to decrease surface energy which results in particle fusion.

Fusion in the liquid phase can include full melting, liquid-phase sintering, and indirect fusion. Generally, metal, ceramic, and polymer materials capable of being melted and re-solidified can be used for these approaches. With full melting, particles are fused by fully melting them with a high-power energy source such as a laser or electron beam. Liquid-phase sintering uses a mixture of two polymer materials, in which the thermal source melts a lower-melting-temperature constituent, but a higher-melting-temperature constituent remains solid. The lower "melting" temperature constituent is sometimes referred to as the binder particle and the higher melting temperature constituent as the structural particle. An example of indirect fusion is a material comprising structural particles (e.g., a metal) coated with a binder (e.g., a polymer). Exposure to the thermal source melts the binder, thus inducing fusion, while the structural particle remains solid.

In some embodiments, a "modified" material or surface can be formed from a texturizing process. Texturizing encompasses any process that can be used to change the surface of the material including machining processes such as grinding or polishing. Texturizing also encompasses solvent polishing processes that can be used to change the surface of the material.

In some embodiments, a "modified" material or surface can be formed from a surface smoothing process of a material. the surface smoothing process can include a powdered or non-powdered material. For example, Fused Deposition Modeling (FDM) processes may deposit traces of material that can create a rippled surface. It has been shown that heating and solvent exposure can smooth these surfaces. In some instances, the smoothing process can involve an additive manufacturing process, but not a powdered material. There, however, may also be applications that can use a rough surface that was not created by additive manufacturing, such as a polymer that was machined. In both these cases, the exposure to heat or solvent needs to be monitored to avoid deforming the material and losing the geometric accuracy. The methods disclosed herein would be suitable for monitoring such surface smoothing process.

In general, this disclosure relates to any kind of densification process such as by sintering, smoothing, or melting effected by a high-energy beam from a suitable source or a texturizing process effected by an energy source or a solvent. The energy source can be selected from a projected image, a laser beam, or an infrared source which increases the temperature of the material being processed. The energy source can be stationary or moving. For example, the method can include exposing a first layer of the material to an electromagnetic beam or image. In some embodiments, the electromagnetic beam or image does not move relative to the first layer of the polymer. In other embodiments, the method can include scanning an electromagnetic beam or image across the first layer of the polymer according to a given path. In certain embodiments, the electromagnetic beam can be provided by a collimated or substantially (nearly) collimated light source, a focused light beam, or a projected image.

The optical properties of the material's surface are related to its structural properties and/or its chemical composition such that when a beam of light reaches the material's surface, part of it will be reflected by the surface directly, while the rest will be refracted and transmitted into the material. Such structural properties can include the phase, density, surface roughness, or porosity of the material, and will thus depend on the material and/or degree which the material is being processed. For a sintering process, the modified surface can be defined by Ra, surface smoothness. "Smoothness" as used herein refers to the planarity of a surface. Smoothness is measured by Ra, a surface texture parameter well known in the art and is the arithmetical mean deviation of the profile. Ra is the area between the roughness profile of a surface and the mean line of the surface. In other words, Ra is the integral of the absolute value of the roughness profile height over the evaluation length. For a melting process, the modified surface can be defined by the presence of a homogenous liquid phase. Other modified surfaces can be defined by the porosity of the surface.

One object of the present disclosure is to provide a method that utilizes changes that take place in the reflection characteristics of the material due to an applied energy or solvent where the change in reflection characteristics of the material is due to changes in its surface structural properties. Accordingly, the methods disclosed herein can include directing light from a light source at an incident angle with respect to the at least partially modified surface of the material. Preferably, the incident light is at an angle or wavelength maximizes the change in reflectivity from the modified and unmodified material. In some embodiments, the incident light can be at an angle such that a modified surface (such as a sintered, melted, smooth, or graded surface) of the material reflects negligible amounts of the light. The contrast in also true in which the incident light can be at an angle such that a modified surface (such as a sintered, melted, smooth, or graded surface) of the material reflects maximum amounts of the light. In some instances, it may be desirable to choose a wavelength of incident light at which the processed (such as fused, sintered, or melted) material is at least partially transparent as reflected signal can be obtained from sub-surface defects such as pores in the unprocessed material.

In some embodiments, the reflectivity of the exterior surface of the material is monitored during the smoothing process. Prior to the smoothing process, the exterior surface of the material is rough, thereby exhibiting a diffuse reflectivity, where light rays from a single incoming direction are reflected into a broad range of outgoing directions. The smoothing process, however, can increase the planarity and/or glossiness of the exterior surface, thereby increasing the specular reflectivity of the exterior surface.

The path of the incident light from the light source can be synced with the energy source. For example, the incident light can be configured to provide active tracking of the energy source's path in order to follow the material's surface. In other embodiments, the energy source's path can be programmed in a control so that a programmed path of the incident light tracks the programmed path of the energy source. In some embodiments, the timing of the energy source and the incident light can be delayed.

The light source can be a laser beam, a focused light beam (such as from a lamp having reflectors that focus its energy onto the target plane), or a projected image. Preferably, the light source is a collimated or substantially (nearly) collimated light source. The light source can include a broad spectrum of wavelengths, such as a broad spectrum of ultraviolet light. In some instances, the energy source and the light source can be the same. For example, the energy source can include a projected image that provides energy (for modifying the surface of the material) and the incident light. In these embodiments, the projected image may have a given shape and may be stationary. In other instances, the energy source and the light source are different.

Heating (i.e., source of energy) and/or the incident light can be performed by projecting an image from an image projector onto a surface area of the layer of material. Particularly, in the methods disclosed herein, Large Area Projection Sintering (LAPS), can be utilized for heating and/or the incident light source. LAPS uses a visible light projector to heat subsections or an entire desired shape in the XY-plane in a single exposure utilizing a high power projection system. Additive manufacturing processes using LAPS is disclosed in PCT/US2018/040624 and U.S. Ser. No. 15/230,651, the disclosures of which are hereby incorporated by reference in their entirety. In some embodiments, the LAPS processing system includes a platform for supporting a layer of material and at least one image projector, where the at least one image projector further includes, a light source, a digital light switch to modulate the light source based upon a digital signal to produce at least one image, at least one lens coupled to the digital light switch. In the material processing system of the present invention, the at least one image projector is configured to project the at least one image through the at least one lens and onto a surface area of the layer of material, wherein an intensity of the at least one image is sufficient to heat the layer of material to a desired temperature.

The system may further include a heated chamber to preheat the material prior to exposing the material to the light from the projector. The light from the projector may be provided through a projection window positioned over the material. The system may further include a thermocouple or other temperature measurement device, such as a pyrometer or an infrared camera to measure the surface temperature from a distance or a thermistor which could be positioned within the material to measure the temperature of the material during the process. In the present disclosure, a blade or roller may be used to spread new uniformly smooth layers of the material over an aluminum platform. In one embodiment of the present disclosure, the high intensity projector provides a concentrated 7.3 W of optical power onto a 3.7 $cm^2$ exposure area. As such, the projection system is capable of exposing an entire layer of material simultaneously over the course of a few seconds. This method allows for longer exposure times without compromising the overall build time, which enable improved properties for processing of a wider variety of materials.

In a particular embodiment, a plurality of image projectors may be used to simultaneously project different images onto different surface areas of the layer of material, thereby increasing the processed area. For example, multiple projectors can be arranged in a 1D array (straight line) and scanned in 1 direction over the entire bed. In addition, the image may be comprised of a plurality of partial images and the image projector may be controlled to project each of the partial images onto a different surface area of the layer of material, thereby forming a complete image. In other embodiments, a single projector can be scanned in 1 direction over the entire bed.

While the LAPS technology has been demonstrated as one possible implementation path, it is considered to be within the scope of the present invention to utilize other means of heating (i.e., other sources of incident light) the polymer material. For example, heating can be performed by selectively illuminating an array of lights (e.g., small LEDs or laser) to create an illuminated region which is then projected as incident light onto the surface of the material. In other embodiments, heating can be performed by scanning a point source (such as a laser) at high rate of speed repeatedly over a surface of the material so that it acts more like a lower intensity constant exposure. Other forms of energy source include a laser beam, a scanning mirror galvanometer or a lamp. Any combination of the energy sources disclosed herein can be used sequentially (in any order) or simultaneously in the methods disclosed. For example, a combination of laser and scanning mirror galvanometer can be used as an energy source.

In contrast with conventional sintering techniques known in the art, in the proposed material processing system, the incident light is projected over the course of a few seconds, instead of a few milliseconds, thereby allowing sufficient time for densifying, fusing, melting, and/or condensing the polymer material. For example, the incident light is projected greater than 100 ms, greater than 1 s, greater than 2 s, greater than 5 s, greater than 7 s, greater than 8 s, greater than 10 s, greater than 12 s, greater than 15 s, from 100 ms to 30 s, from 1 s to 15 s, or from 1 s to 10 s. The extended time also allows for monitoring (including in-situ monitoring) and control systems to be implemented. For example, the intensity of the incident light can be controlled based on the temperature of the polymer material in each spot. The incorporation of monitoring and control systems improves the quality of the resulting components by ensuring that every location within the material layer has been heated in accordance with the correct thermal profile.

In the projected incident light (e.g., the projected image), varying levels of power can be projected onto the material. In some embodiments, the incident light is projected at a power level from 1 $W/cm^2$ to 50 $W/cm^2$, from 1 $W/cm^2$ to 30 $W/cm^2$, from 1 $W/cm^2$ to 15 $W/cm^2$ or from 2 $W/cm^2$ to 15 $W/cm^2$. In specific examples, the methods include projecting an image over a 100 ms to 10 s time span at from 1 $W/cm^2$ to 50 $W/cm^2$ from an image projector (LAPS processing system) onto a surface area of the layer of material.

In some embodiments of the manufacturing process, incident light at a substantially constant power level is incident on a material and a lateral layer of the part is fabricated by simultaneously projecting the incident light on a subsection or over an entire surface area of the material to densify, fuse, melt, and/or texturize the material optionally followed by cooling, until the entire layer has been processed. When one layer is complete, the surface of the powder bed is lowered, another layer of powder is spread over the previous, now sintered layer, and the next layer is scanned. As a layer is completed, another layer of powder is deposited on top of the previous layer, either by a blade, a roller mechanism or some other uniform powder spreading technique and the process is repeated until a complete component (sintered article) is formed.

More specifically, layerwise sintering can be performed by dispensing a layer of material over a platform to a desired thickness, and then directing energy from an energy source at the locations of the material layer that correspond to the cross-section of the object(s) to be formed in that layer. The material at the irradiated locations is heated so as to fuse, for example by solid-phase sintering into a mass. Upon completion of fusing the layer, a subsequent layer of material is placed over the prior layer, supported by both the fused and unfused polymer material, and the irradiation is repeated to define the cross-section of the object to be formed in the next layer. The process is repeated until the object is completely formed.

As described herein, the methods can be used to monitor or control a manufacturing process by determining when a variation in surface characteristics takes place. Such surface characteristics correlate to the processing condition of the material and as described herein, can include density, roughness, or porosity on or beneath a surface of the material being processed. Accordingly, the methods disclosed herein can include measuring one or more predetermined properties of light reflected to a detector from the at least partially modified surface, wherein the predetermined properties correlate to a processing condition of the material. The predetermined properties can include the number of reflective spots, the spacing of light, or the intensity of light reflected from the surface. The measured reflectance can be used to provide quantitative data regarding the surface characteristics of the material, or can be compared to a range of acceptable reflectance which has been predetermined by measuring the reflectance of a set of control samples with known surface characteristics. It is preferable that the measurement of the reflectance be taken at a plurality of reflection angles so as to obtain more data.

The incident light on the surface and the detector can be arranged (positioned) so that the light reflected off the fully processed surface will not reflect to the detector. This is possible when the incident light is not normal to the fully processed surface and that the angle of the detector is not equal to the angle of the incidence. Accordingly, the methods disclosed herein can include determining that the material is fully processed when a measured predetermined property of the light reflected is about zero at an incident angle that is not normal to the fully processed material and the incident angle is not equal to an angle of the detector. In some cases, both the incident light and the detector may be positioned in the same plane, but this is not required.

In other cases, the incident light on the surface and the detector can be arranged so that light reflected from the fully processed material is reflected into the detector. In these cases, increasing property of light measured correlates to improvement in the processing condition. It has been found in some cases, that fully processed materials (such as smooth, sintered, or melted materials) reflect greater amounts of light, while unprocessed or partially processed materials (such as rough, unmelted, or unsintered materials) scatter light to a greater degree, with the degree of scattering differing at each wavelength. The methods disclosed herein can include determining that the material is fully processed when a measured predetermined property of the light reflected is maximum at an incident angle equal to an angle of the detector. In these cases, the incident light, the normal, and the detector are in the same plane.

The methods disclosed herein can include measuring the light reflected at various time points during the manufacturing process. For example, the method can include measuring the light reflected or lack thereof at a first timepoint and at a second timepoint. As described herein, the property of the light reflected can directly relate to the extent to which the surface is modified. Accordingly, the methods can be used to monitor changes in the property (example intensity) of the light reflected, which can be correlated to changes in the surface characteristics of the material.

A preliminary step in the methods disclosed herein can include the compilation of a calibration matrix of reflectance data correlated with surface characteristics of a group of control samples which are made of the material being examined. The control samples preferably range over a variety of known surface characteristics such as roughness, densities, and/or porosities. The reflectance data will preferably be accumulated for a plurality of angle of reflection. Generally, the larger and more comprehensive the calibration matrix is, the more accurate will be the assessment of the test sample to be characterized from the reflectometer measurements.

The light reflected from the material can be detected and measured using a detector. The detector is not limited and can be any suitable detector that detects light reflected from the surface. In some examples, the detector can be selected from a thermal camera, an optical camera, a line camera, or a point detector such as those including a photodetector/photodiode. In some cases, the detector can include a high speed, high resolution camera. The detector can be configured to receive reflected light (electromagnetic radiation) and converted to images captured by the camera, derive image data from the images, and analyze the image data. The images of the material's surface created during the manufacturing process can be captured by the camera in real-time. In some embodiments, the images can be captured periodically or at pre-set intervals. The captured images can be fed back to a processing and control unit of the detector where image data is derived from the images. In some embodiments, the image data may include various surface characteristics such as phase, roughness of the surface, or porosity of the material. In some embodiments, the camera can monitor for example, sintering progression as the pixels change intensity values as the powder bed's reflective and refractive properties change during subsequent heating, melting and densification. In some cases, the detector can be moveable over the surface from which reflectance measurements are taken so that the angle of reflection can be varied. The compiled reflectance can be taken over a broad range of the electromagnetic spectrum such as the ultraviolet spectrum and at a plurality of angles of reflection. The measured reflectance can be compiled in a calibration matrix, which will typically comprise plotting the reflectance values in a graphical plot, or storing the reflectance values in a look-up table of a computer software program.

In some embodiments, the detector can analyze the image data including inputting the image data into a statistical process control module. In certain embodiments, analyzing the image data includes comparing the image data to pre-determined control limits. For example, the image data can be fed into a statistical process control module and analyzed to determine if the material's surface is deformed. The image data can then be plotted on one or more graphs with pre-determined control limits. The control limits may be tailored to the specific powder material or properties of the material including phase, surface roughness, or porosity.

Data that fall within the pre-determined control limits indicates that everything is operating as expected. Any variation within the control limits is likely due to a common cause—the natural variation that is expected as part of the manufacturing process. If data falls outside of the predetermined control limits, this indicates that an assignable cause is likely the source of the product variation, and something within the process should be changed to fix the issue before defects occur. If it is determined that the captured image data of the surface fall outside of the control limits, an alert can be generated. In some cases, at higher resolution, there can be some spatial noise due to the surface variation of individual particles. This may require some degree of statistical analysis and or spatial averaging.

In some embodiments, the methods described herein provide for closed loop feedback of surface image data that can be utilized in the process operation so that abnormalities can be addressed before defects occur, or at least before the entire manufacturing cycle is run. For example, the method can include adjusting one or more processing parameters of the energy source in response to the reflected electromagnetic radiation detected. The step of adjusting one or more processing parameters can occur in real-time. Adjusting the processing parameters can include taking a corrective action in response to the image. The corrective action may include pausing operation of the system and calibrating, adjusting or replacing a component of the system, and resuming operation. In some embodiments, the corrective action may include removing the component from the system and initiating a new cycle.

In some examples, the methods described herein can be used in a laser sintering additive manufacturing system. In some embodiments, the corrective action can include, but are not limited to, laser-related parameters (e.g., laser power, spot size, spot geometry, shape, pulse duration and frequency or variance thereof in a temporal or spatial domain), scan-related parameters (e.g., scan pattern, speed, and spacing), powder-related parameters (e.g., particle shape, size and distribution, powder bed density, layer thickness, material properties, and uniform powder deposition), and temperature related parameters (powder-bed temperature, powder material supply temperature, temperature uniformity, and temperature monitoring).

In some embodiments, the method can be used to monitor the manufacturing process for quality assurance purposes. For example, the method may not include a feedback to the control parameters.

EXAMPLE

The following example is set forth below to illustrate the methods and results according to the disclosed subject matter. This example is not intended to be inclusive of all aspects of the subject matter disclosed herein, but rather to illustrate representative methods, compositions, and results. This example is not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1

The present example provides a lower cost, higher speed/resolution, method of tracking the changes in the material by responding to the changes in the volume and surface of the material rather than the temperature. Described are surfaces that are not smooth but that becomes smoother during processing. While this could be applied to many surface types, this example is particularly relevant to a powder layer. In the example, a light is used to illuminate the area of interest. A standard point source is acceptable though performance can be improved by utilizing a more highly collimated light. The light should be incident on the area of interest at an angle such that little or no light will reflect into the detector off a smooth surface. In this condition, the detector will still see reflected light off a rough (diffuse) surface because the surface roughness provides a variety of surface angles of which many will be create the necessary incident angle to be reflected back to the detector. Other light may pass through particles and be absorbed or reflected off other surfaces after one or more reflections. Similar reflections could also come from bubbles or other defects inside a surface.

Processes such as melting or sintering allows the particles to change shape and evolve toward a flat surface. As this process occurs, less surface area will have the angle required to reflect the incident light to the detector—reducing the signal. The change in light reaching the detector over time can be correlated to the condition of the surface or powder of interest. The brightness over an area can be correlated to a degree of sintering over an area or to specific defects/features on the surface. This system can then be used to monitor in real time the status of the process evolution, verify sintering state, provide process feedback, flag areas of interest where print errors may have occurred, and/or geometry before and after sintering. This technique could be applicable to any powder bed fusion technology and for almost any wavelength of light given the availability of an appropriate detector.

Summary: This example provides an in-situ means to control the sintering process in powder bed fusion additive manufacturing (AM) methods, such as large area projection sintering. The control signal is provided by a sensor capable of capturing reflected light over a large area (such as a thermal or optical camera). The sintering process can be controlled down to a single pixel or voxel by evaluating the intensity of light at each pixel in the detector. This information can then be used in a feedback control loop to the sintering process.

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

What is claimed is:

1. A method for monitoring or controlling an additive manufacturing process of a powder material, comprising:
    a) directing a solvent from a solvent source or energy from an energy source on a surface of the powder material wherein the powder material is a polymer material, a fibrous material, or a fabricated composite material to form an at least partially modified surface;
    b) directing light from a light source at an incident angle with respect to the at least partially modified surface;
    c) measuring one or more predetermined properties of light reflected to a detector from the at least partially modified surface, wherein the predetermined properties correlate to a processing condition of the powder material; and wherein the step of measuring comprises a transition of a diffusive reflection of the light to a specular reflection of the light;

d) determining that the powder material is fully processed when a measured predetermined property of the light reflected reaches a target value; wherein the target value is about zero at an incident angle that is not normal to a fully processed material and the incident angle is not equal to an angle of the detector, and e) if the measured predetermined property of the reflected light has not reached the target value, adjusting a processing parameter of the additive manufacturing process in response to the measured predetermined property until the target value is reached.

2. The method of claim 1, wherein the additive manufacturing process is selected from a melting process, a sintering process, or a texturing process.

3. The method of claim 1, wherein the energy source in step (a) is selected from an electromagnetic beam or an image.

4. The method of claim 3, wherein the energy source is an image from an image projector, a laser beam, an infrared source, or an array of LEDs or lasers.

5. The method of claim 1, wherein the light source is a collimated light source, a focused light beam, or a projected image.

6. The method of claim 1, wherein the detector is selected from a thermal camera, an optical camera, a line camera, or a point detector.

7. The method of claim 1, wherein the predetermined property of light in step (c) is selected from an amount of reflective spots, a spacing of the light, or an intensity of the light.

8. The method of claim 1, wherein the processing condition is selected from density, roughness, or porosity on a surface of the powder material.

9. A method for monitoring or controlling a melting or sintering additive manufacturing process of a powder material, comprising:
   a) projecting energy from an energy source on a surface of the powder material, wherein the powder material is a polymer material to form an at least partially sintered or melted surface,
   b) directing light from a light source at an incident angle with respect to the at least partially sintered or melted surface,
   c) measuring one or more predetermined properties of the light reflected to a detector from the at least partially sintered or melted surface, wherein the predetermined properties correlate to a processing condition of the powder material; and wherein the step of measuring comprises a transition of a diffusive reflection of the light to a specular reflection of the light;
   d) determining that the powder material is fully sintered or melted when a measured predetermined property of the light reflected reaches a target value, wherein the target value is about zero at an incident angle that is not normal to a fully processed material and the incident angle is not equal to an angle of the detector, and
   e) if the measured predetermined property of the reflected light has not reached the target value, adjusting a processing parameter of the additive manufacturing process in response to the measured predetermined property until the target value is reached.

10. The method of claim 9, wherein the energy source in step (a) is selected from an electromagnetic beam or an image.

11. The method of claim 10, wherein the energy source is an image from an image projector, a laser beam, an infrared source, or an array of LEDs or lasers.

12. The method of claim 9, wherein the detector is selected from a thermal camera, an optical camera, a line camera, or a point detector.

13. The method of claim 9, wherein the processing parameter comprises an intensity, spot size, pulse frequency, shape, pulse duration, or spot geometry of all or part of the energy source or variance thereof in a temporal or spatial domain.

14. A method for monitoring or controlling surface treatment of a material, comprising:
   a) directing a solvent from a solvent source or energy from an energy source on an exterior surface of the material to reduce or eliminate surface defects and smooth the exterior surface of the material;
   b) directing light from a light source at an incident angle with respect to the exterior surface of the material;
   c) measuring one or more predetermined properties of light reflected to a detector from the exterior surface of the material, wherein the predetermined properties correlate to a planarity of the material; and wherein the step of measuring comprises a transition of a diffusive reflection of the light to a specular reflection of the light;
   d) determining that the material is planar when a measured predetermined property of the light reflected reaches a target value; wherein the target value is about zero at an incident angle that is not normal to a fully processed material and the incident angle is not equal to an angle of the detector, and
   e) if the measured predetermined property of the reflected light has not reached the target value, adjusting a processing parameter of the surface treatment in response to the measured predetermined property until the target value is reached.

15. The method of claim 14, wherein the energy source in step (a) is selected from an electromagnetic beam or an image.

16. The method of claim 1, wherein step b) comprises choosing a wavelength at which the at least partially modified surface is at least partially transparent.

17. The method of claim 1, wherein the steps e) occurs in real-time and comprises a corrective action.

18. The method of claim 9, wherein step b) comprises choosing a wavelength at which the at least partially modified surface is at least partially transparent.

19. The method of claim 9, wherein the steps e) occurs in real-time.

20. The method of claim 14, wherein the steps e) occurs in real-time.

* * * * *